(12) United States Patent
Uozumi et al.

(10) Patent No.: US 8,184,008 B2
(45) Date of Patent: May 22, 2012

(54) ON-BOARD WARNING APPARATUS AND WARNING METHOD

(75) Inventors: Shigeyasu Uozumi, Toyota (JP); Kenichi Ohue, Toyota (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 355 days.

(21) Appl. No.: 12/311,555

(22) PCT Filed: Oct. 10, 2007

(86) PCT No.: PCT/IB2007/002999
§ 371 (c)(1),
(2), (4) Date: Apr. 3, 2009

(87) PCT Pub. No.: WO2008/044119
PCT Pub. Date: Apr. 17, 2008

(65) Prior Publication Data
US 2010/0007480 A1    Jan. 14, 2010

(30) Foreign Application Priority Data

Oct. 13, 2006 (JP) ................................. 2006-280366
Oct. 13, 2006 (JP) ................................. 2006-280367

(51) Int. Cl.
*G08B 23/00* (2006.01)
(52) U.S. Cl. ......... 340/576; 340/575; 340/439; 180/271
(58) Field of Classification Search .................. 340/439, 340/575, 576; 180/271, 272
See application file for complete search history.

(56) References Cited

U.S. PATENT DOCUMENTS

| | | | | |
|---|---|---|---|---|
| 4,565,997 A * | 1/1986 | Seko et al. | .................... | 340/576 |
| 4,953,111 A * | 8/1990 | Yamamoto et al. | ........... | 340/575 |
| 5,311,877 A * | 5/1994 | Kishi | ............................ | 340/576 |
| 5,349,430 A * | 9/1994 | Yamamoto et al. | ........... | 340/903 |
| 5,432,509 A * | 7/1995 | Kajiwara | ...................... | 340/903 |
| 5,574,641 A * | 11/1996 | Kawakami et al. | ........... | 340/576 |
| 6,097,295 A * | 8/2000 | Griesinger et al. | ........... | 340/576 |
| 6,304,187 B1 * | 10/2001 | Pirim | ............................ | 340/576 |
| 6,575,902 B1 * | 6/2003 | Burton | ......................... | 340/575 |
| 7,202,792 B2 * | 4/2007 | Zhang et al. | .................. | 340/575 |
| 7,639,148 B2 * | 12/2009 | Victor | ........................... | 340/576 |

(Continued)

FOREIGN PATENT DOCUMENTS

EP    0 549 909 A2    7/1993

(Continued)

OTHER PUBLICATIONS

Jul. 29, 2008 Office Action issued in Japanese Patent Application No. 2006-280366 (with translation).

*Primary Examiner* — Eric M Blount
(74) *Attorney, Agent, or Firm* — Oliff & Berridge, PLC

(57) ABSTRACT

An on-board warning apparatus of the invention includes an inattentive time measuring device that measures a duration of an inattentive state of a driver; a dozing time measuring device that measures a duration of a dozing state of the driver; a first warning output device that warns the driver when the measured inattentive time exceeds a first predetermined period of time Ta; and a second warning output device that warns the driver when the measured dozing time exceeds a second predetermined period of time Tb. The first predetermined time Ta is shorter than the second predetermined period of time Tb.

15 Claims, 6 Drawing Sheets

U.S. PATENT DOCUMENTS

2001/0054963 A1 * 12/2001 Cheung .................. 340/575
2005/0264426 A1 * 12/2005 Ferrone et al. ............ 340/576

FOREIGN PATENT DOCUMENTS

| | | |
|---|---|---|
| EP | 1 312 499 A2 | 5/2003 |
| JP | B2-2583335 | 2/1997 |
| JP | A-11-339199 | 12/1999 |
| JP | A-2002-219968 | 8/2002 |
| JP | A-2006-151287 | 6/2006 |
| WO | WO 96/16830 A1 | 6/1996 |
| WO | WO 03/070093 A1 | 8/2003 |
| WO | WO 2004/102500 A1 | 11/2004 |

* cited by examiner

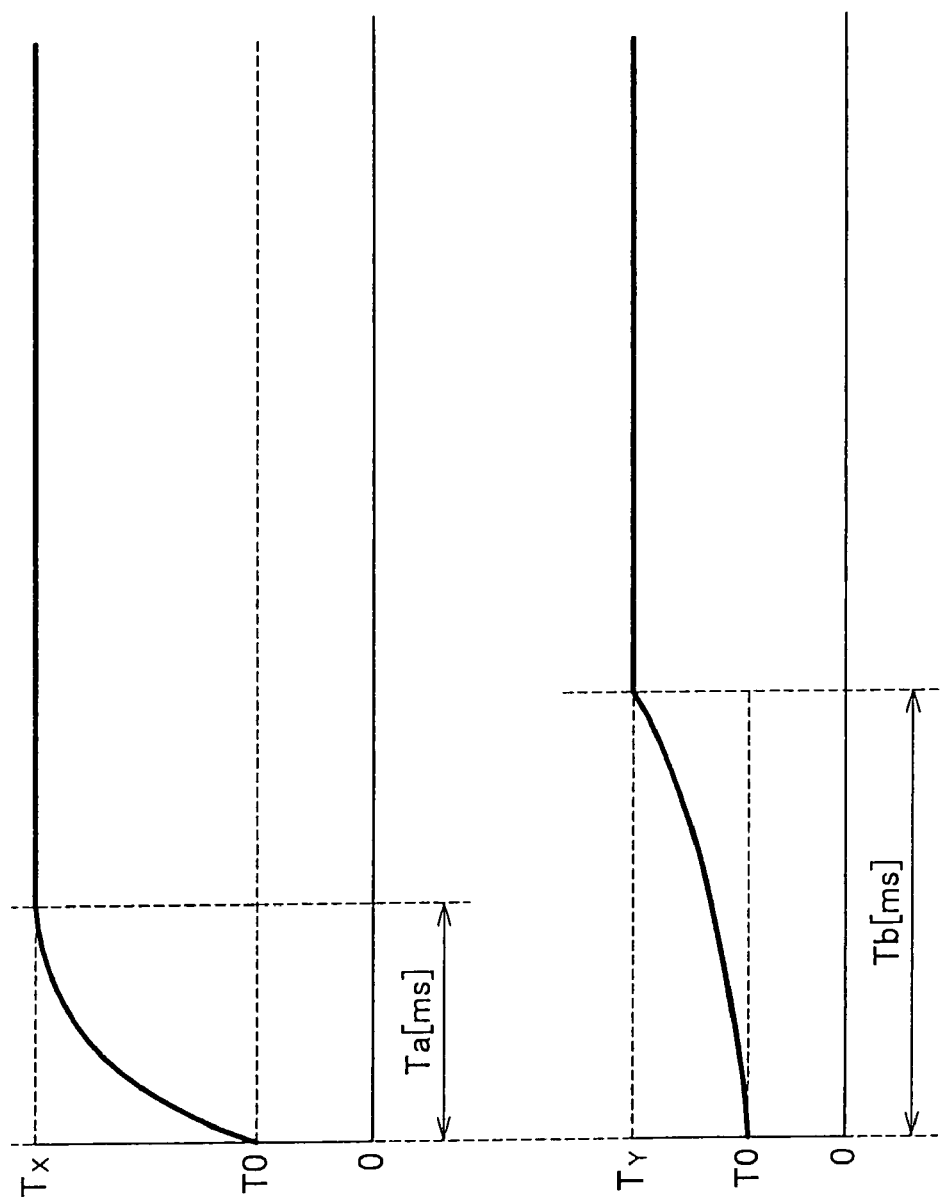

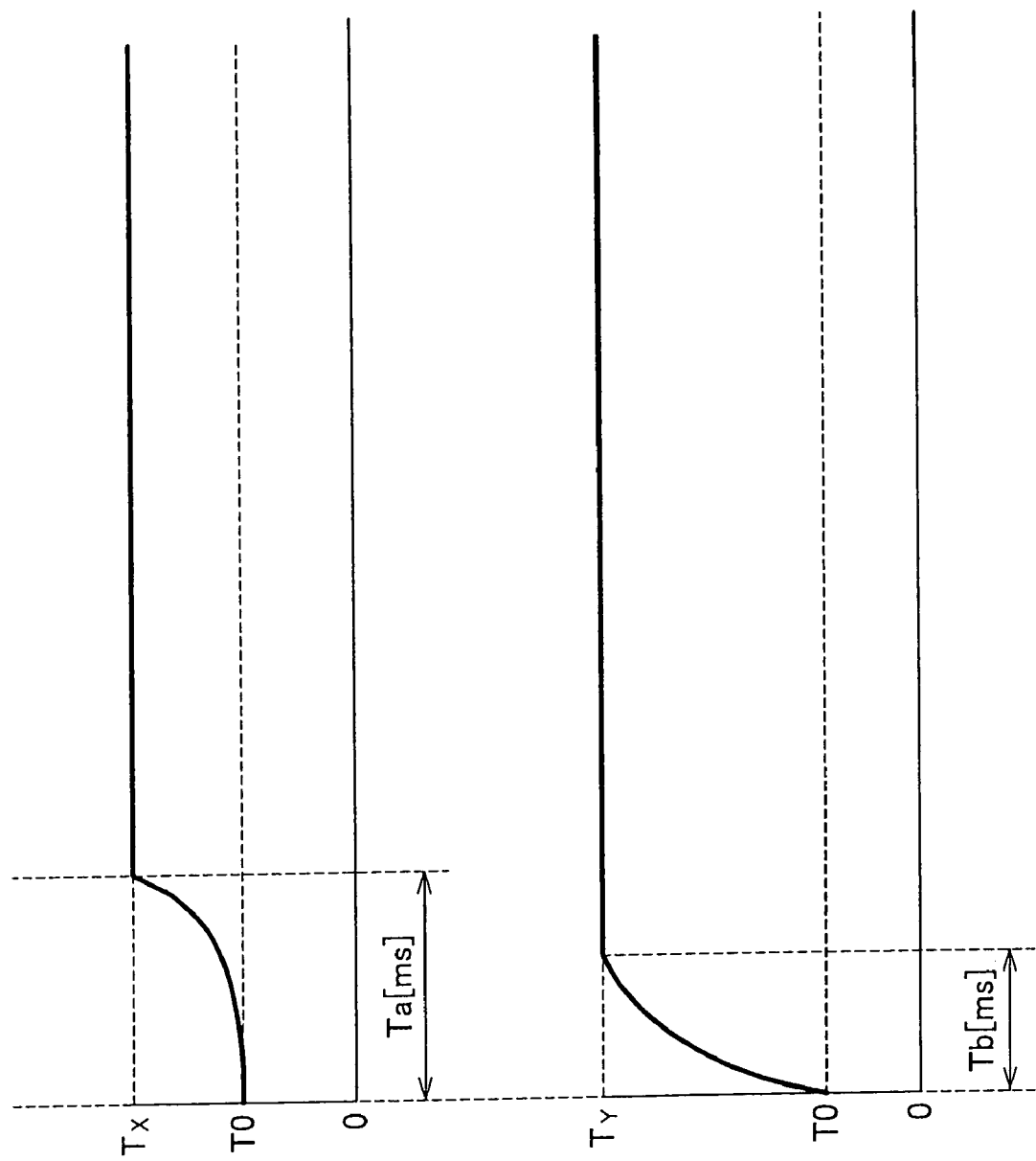

ON-BOARD WARNING APPARATUS AND WARNING METHOD

BACKGROUND OF THE INVENTION

1. Field of the Invention

The invention relates to an on-board warning apparatus and warning method for warning a driver using results from measuring the time for which the driver is inattentive and the time for which the driver is dozing off or the time for which the drive's eyes are closed.

2. Description of the Related Art

Japanese Patent Application Publication No. 2002-219968 (JP-A-2002-219968), for example, describes a warning apparatus that issues a warning when a driver is inattentive or dozing off while driving. This warning apparatus includes driver state detecting means for detecting an inattentive state and a dozing state of the driver; measuring means for measuring the duration of the inattentive state and the dozing state of the driver; vehicle speed detecting means for detecting the vehicle speed; vehicle-to-vehicle distance detecting means for detecting the distance to a leading vehicle; vehicle-to-vehicle time calculating means for calculating the time to the leading vehicle based on the vehicle speed detection value and the vehicle-to-vehicle distance detection value; allowable time setting means for looking up and setting an allowable time corresponding to the vehicle-to-vehicle time calculating value from a table listing allowable times with respect to vehicle-to-vehicle times set beforehand so that the allowable time is the maximum value at a predetermined vehicle-to-vehicle time; and determining means for determining that the driver is inattentive or dozing off while driving when the duration of the inattentive state or the dozing state exceeds the allowable time set value.

Also, Japanese Patent No. 2583335, for example, describes a leading vehicle approaching warning apparatus that includes host-vehicle vehicle speed detecting means for detecting the driving speed of a host vehicle; leading-vehicle vehicle speed detecting means for detecting the driving speed of a leading vehicle; vehicle-to-vehicle distance detecting means for detecting the vehicle-to-vehicle distance between the host vehicle and the leading vehicle; warning issuing means for issuing a warning to the driver when the relative speed of the host vehicle with respect to the leading vehicle becomes equal to or greater than a predetermined allowable relative speed, with respect to the vehicle-to-vehicle distance; and driving state detecting means for detecting when the driver is inattentive or dozing off while driving. This leading vehicle approaching warning apparatus corrects, i.e., lowers, the allowable relative speed when inattentiveness or dozing off while driving is detected, and issues the warning when the relative speed of the host vehicle becomes equal to or greater than that corrected allowable relative speed.

In the invention described in JP-A-2002-219968, the allowable time set value with respect to the duration of the inattentive state or the duration of the dozing state is set according to the vehicle-to-vehicle time. Therefore, the allowable time set value with respect to the duration of the inattentive state and the allowable time set value with respect to the duration of the dozing state are the same values. However, the inattentive state and the dozing state each have different characteristics so the warning timing may not be appropriate with a structure that sets the warning timing with the same determining reference for the inattentive state as it does for the dozing state.

Also, similarly, in the invention described in Japanese Patent No. 2583335, the warning timing when there is a danger of collision is set without taking the respective characteristics of the inattentive state and the dozing state into account so the warning timing may not be appropriate.

DISCLOSURE OF THE INVENTION

This invention thus aims to provide an on-board warning apparatus and warning method capable of issuing a warning at an appropriate warning timing that takes into account the characteristics of an inattentive state of the driver and a dozing state of the driver or a state in which the driver's eyes are closed (hereinafter referred to simply as "closed-eye state").

A first aspect of the invention relates to an on-board warning apparatus that includes an inattentive time measuring device that measures a duration of an inattentive state of a driver; a dozing time measuring device that measures a duration of a dozing state of the driver; a first warning output device that warns the driver when the measured inattentive time exceeds a first predetermined period of time; and a second warning output device that warns the driver when the measured dozing time exceeds a second predetermined period of time. The first predetermined time is different than the second predetermined period of time. That is, the first predetermined time may made be shorter or longer than the second predetermined period of time as appropriate.

A second aspect of the invention relates to an on-board warning apparatus that includes a collision danger determining device that determines whether there is a danger of collision between a host vehicle and an object in front of the host vehicle based on a relationship between a predetermined threshold value and a physical quantity capable of indicating a relative relationship between the host vehicle and the object in front of the host vehicle; a warning output device that warns a driver when the collision danger determining device determines that there is a danger of collision; an inattentive time measuring device that measures a duration of an inattentive state of the driver; a dozing time measuring device that measures a duration of a dozing state of the driver; and a threshold value changing device that changes the predetermined threshold value according to one of the measured inattentive time and the dozing time so that the collision danger determining device more readily determines that there is a danger of collision. An amount of change in the predetermined threshold value for the inattentive time is different than an amount of change in the predetermined threshold value for the dozing time. That is, the amount of change in the predetermined threshold value for the inattentive time may be made greater or less than the amount of change in the predetermined threshold value for the dozing time.

The dozing time measuring device may also measure a duration of a state in which the eyes of the driver are closed as the dozing time.

A third aspect of the invention relates to an on-board warning apparatus that includes an inattentive time measuring device that measures a duration of an inattentive state of a driver; a closed-eye time measuring device that measures a time during which the eyes of the driver are closed; a first warning output device that warns the driver when the measured inattentive time exceeds a first predetermined period of time; and a second warning output device that warns the driver when the measured closed-eye time exceeds a second predetermined period of time. The first predetermined time is different than the second predetermined period of time. That is, the first predetermined period of time may be shorter or longer than the second predetermined period of time.

A fourth aspect of the invention relates to an on-board warning apparatus that includes a collision danger determining device that determines whether there is a danger of collision between a host vehicle and an object in front of the host vehicle based on a relationship between a predetermined threshold value and a physical quantity capable of indicating a relative relationship between the host vehicle and the object in front of the host vehicle; a warning output device that warns a driver when the collision danger determining device determines that there is a danger of collision; an inattentive time measuring device that measures a duration of an inattentive state of the driver; a closed-eye time measuring device that measures a time during which the eyes of the driver are closed; and a threshold value changing device that changes the predetermined threshold value according to one of the measured inattentive time and the closed-eye time so that the collision danger determining device more readily determines that there is a danger of collision. An amount of change in the predetermined threshold value for the inattentive time is different than an amount of change in the predetermined threshold value for the closed-eye time. That is, the amount of change in the predetermined threshold value for the inattentive time may be made greater or less than the amount of change in the predetermined threshold value for the closed-eye time.

The inattentive time measuring device may also measure a duration of a state in which the driver is not facing forward as the inattentive time.

A fifth aspect of the invention relates to an on-board warning apparatus that includes a device that detects an inattentive state of a driver; a device that detects at least one of a dozing state of the driver and a state in which the eyes of the driver are closed; a first measuring device that measures a duration of the inattentive state of the driver; a second measuring device that measures at least one of a duration of the dozing state of the driver and a time during which the eyes of the driver are closed; and a warning device that issues a warning to the driver. The period of time from the time that the inattentive state is detected until time that the warning is issued differs from the period of time from the time that at least one of the dozing state of the driver and the state in which the eyes of the driver are closed is detected until the time that the warning is issued.

A sixth aspect of the invention relates to a warning method that includes detecting an inattentive state of a driver; detecting at least one of a dozing state of the driver and a state in which the eyes of the driver are closed; measuring a duration of the inattentive state of the driver; measuring at least one of a duration of the dozing state of the driver and a time during which the eyes of the driver are closed; and issuing a warning to the driver. The period of time from the time that the inattentive state is detected until time that the warning is issued differs from the period of time from the time that at least one of the dozing state of the driver and the state in which the eyes of the driver are closed is detected until the time that the warning is issued.

With respect to the fifth and sixth aspects of the invention, there may be by chance a case in which the period of time from the time the inattentive state is detected until the warning is issued happens to match the period of time from the time that at least one of the dozing state of the driver and the state in which the eyes of the driver are closed is detected until the warning is issued. However, what is important is that the warning be output reflecting the rates of response of the driver in the inattentive state, the dozing state, and the state in which his or her eyes are closed.

According to the invention, an on-board warning apparatus can be obtained which is capable of issuing a warning at an appropriate warning timing that takes into account the characteristics of an inattentive state and a dozing state or a closed-eye state of the driver.

BRIEF DESCRIPTION OF THE DRAWINGS

The foregoing and further objects, features and advantages of the invention will become apparent from the following description of exemplary embodiments with reference to the accompanying drawings, wherein like numerals are used to represent like elements and wherein:

FIGS. 5A and 5B are graphs showing the manner of change in a predetermined threshold value Th according to the inattentive time and the closed-eye time; and FIGS. 6A and 6B are graphs showing the manner of change in the predetermined threshold value Th according to the inattentive time and the closed-eye time according to a fourth example embodiment of the invention.

DETAILED DESCRIPTION OF THE EMBODIMENTS

First Example Embodiment

Figure 1:
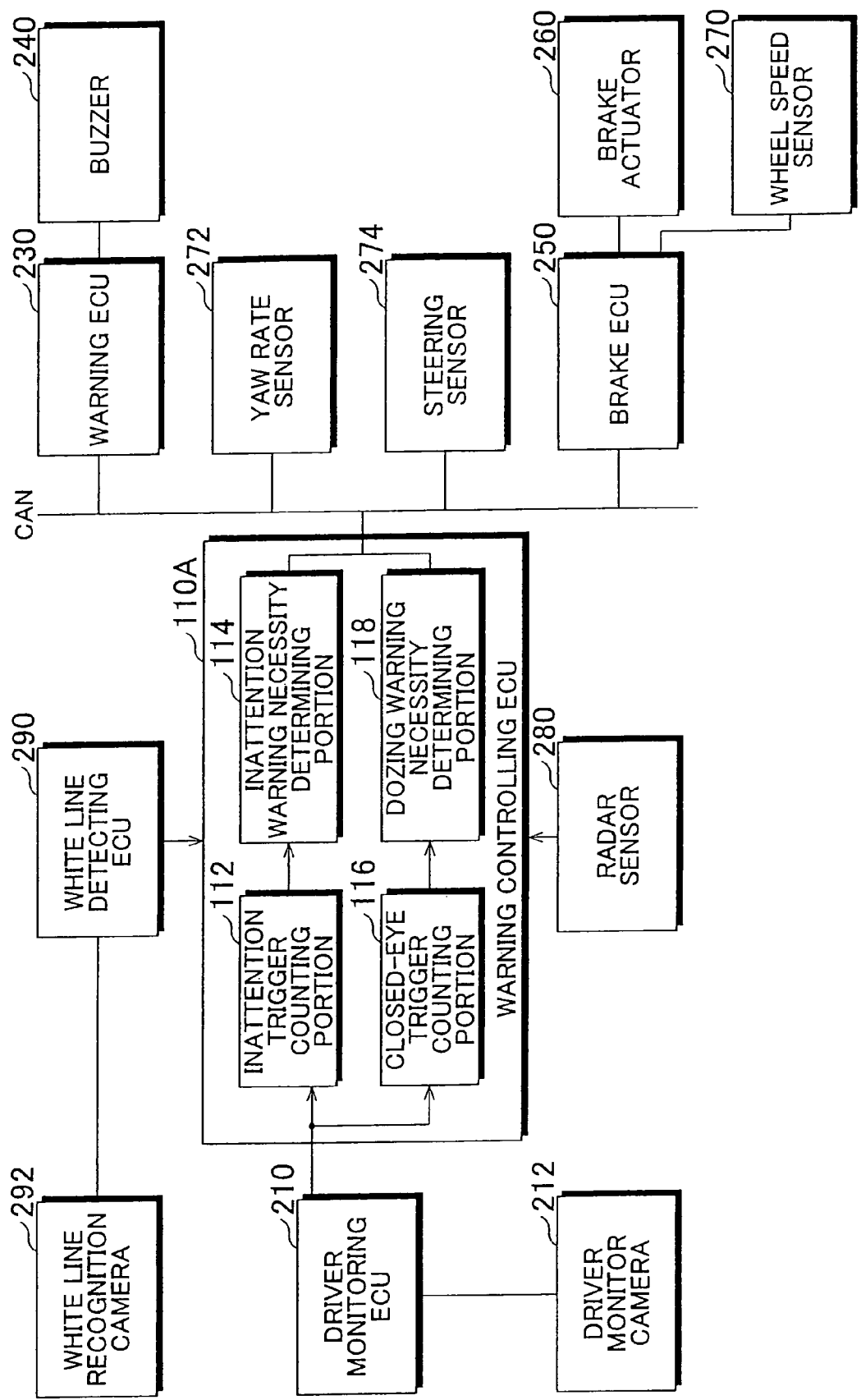
FIG. 1 is a system block diagram which shows an example of the main structure of a warning system that includes an on-board warning apparatus according to a first example embodiment of the invention.

FIG. 1 is a system block diagram which shows an example of the main structure of a warning system that includes an on-board warning apparatus according to a first example embodiment of the invention. The on-board warning apparatus in this example embodiment includes a warning controlling ECU 110A, a driver monitoring ECU 210, a driver monitor camera 212, a warning ECU 230, and a buzzer 240.

The warning controlling ECU 110A includes various hardware such as a CPU that is structured around a suitable processor or microcomputer and performs various processes which will be described later, ROM that stores programs and data used to perform those various processes, readable/writable RAM that stores calculation results and the like, a timer, a counter, an input interface, and an output interface, and the like. The other ECUs 210 and 230 may have similar hardware structures but of course have different programs and data (software) stored in the ROM according to the different processes.

The warning controlling ECU 110A is provided with function blocks that realize main functions. These function blocks include an inattention trigger counting portion 112, an inattention warning necessity determining portion 114, a closed-eye trigger counting portion 116, and a dozing warning necessity determining portion 118.

The driver monitoring ECU 210 is connected via an appropriate bus to the warning controlling ECU 110A and the driver monitor camera 212 is connected to this driver monitoring ECU 210. Also, a white line detecting ECU 290 is connected via an appropriate bus to the warning controlling ECU 110A and a white line recognition camera 292 is connected to this white line detecting ECU 290. Further, a radar sensor 280 is connected via an appropriate bus to the warning controlling ECU 110A. Also, a warning ECU 230 is connected via a bus that supports CAN (controller area network) to the warning controlling ECU 110A, and a buzzer 240 is connected to this warning ECU 230. Moreover, a brake ECU 250 is connected via a bus that supports CAN to the warning controlling ECU 110A and a brake actuator 260 and a wheel-side sensor 270 are connected to the brake ECU 250. Also, in the example shown in the drawing, a yaw rate sensor 272 and a steering sensor 274 are connected via a bus that supports CAN to the warning controlling ECU 110A. Incidentally, these connections do not have to be wired. Some or all of these connections also may be realized by radio channel. Also, the ECUs 110, 210, and 230 are structured as separate units for convenience. However, some or all of the functions of a given ECU may be realized by another ECU, or some of the functions of a given ECU may also be realized by a separate new ECU.

The white line recognition camera 292 is mounted in a suitable location on the vehicle so that it can capture the lane boundary line on the road on which the vehicle is traveling (the white line in this example embodiment is a white line but it may be set appropriately to a lane boundary line color suitable for a given country). The white line recognition camera 292 may be arranged to capture the road in front of the vehicle and/or arranged to capture the road in back of the vehicle. The white line detecting ECU 290 detects the position of the lane boundary line by processing the image from the white line recognition camera 292. Any one of various methods may be used to detect the lane boundary line. For example, a method to detect the lane boundary line by normal edge processing may be used or a method using morphology calculations may be used.

The radar sensor 280 may be arranged near the front grill or in the front bumper of the vehicle, for example, so that it monitors objects in front of the vehicle. The radar sensor 280 emits detection waves and detects the distance from an object in front of the host vehicle to the host vehicle, as well as the direction of the object in front of the host vehicle with respect to the host vehicle, by receiving those detection waves that have reflected off of an object (typically a leading vehicle) in front of the host vehicle within the detection zone of the radar sensor 280. Also, on a curved road, the course in front of the host vehicle may be corrected using output signals from the yaw rate sensor 272 and the steering sensor 274. The detection waves emitted from the radar sensor 280 may be light waves (such as laser waves), radio waves (such as millimeter waves), or sound waves (such as ultrasonic waves). Also, a plurality of the radar sensors 280 may also be arranged to monitor the rear and/or sides of the vehicle. Further, instead of or in addition to the radar sensor 280, an image sensor may be used to monitor the front and/or rear and/or sides of the vehicle.

The driver monitor camera 212 has a color or infrared sensitive CCD (charge-coupled device) sensor array, for example. The driver monitor camera 212 is mounted in an appropriate location in the vehicle so that it can capture the front of the driver (e.g., the front of the driver's face). For example, the driver monitor camera 212 is arranged on the dashboard of the instrument panel, on the steering column, or on the cabin mirror or the like of the vehicle. The driver monitor camera 212 captures an image of the face of the driver (hereinafter referred to as "face image") in real time while the driver is driving the vehicle, and may supply that face image to the driver monitoring ECU 210 typically in 30 fps (frames per second) stream format.

The driver monitoring ECU 210 processes the face image input as needed from the driver monitor camera 212 and detects whether the face of the driver is facing forward. There are many various methods for detecting whether the face of the driver is facing forward based on the image processing. Any appropriate method may be used. For example, the current position of the driver (i.e., the orientation of the face) can be detected by comparing the matching degree between the position or orientation of each part of the face that has been captured as described above and the position or orientation of those same parts of the face in pre-stored positions (such as a position when the driver is facing forward or positions when the driver is looking left, right, up, and down). Face orientation may be represented by a rotational angle around three axes, one of which represents the face facing forward when the driver is in the proper position, for example. When the face orientation is off by a predetermined reference or more with respect to the front, it is determined that the driver is not facing forward. The driver monitoring ECU 210 makes the foregoing determination for each image frame or for each set of a predetermined number of continuous image frames, and supplies the determination results to the warning controlling ECU 110A for each determination cycle. In this example, the driver monitoring ECU 210 supplies a trigger signal indicating that the face of the driver is not facing forward (hereinafter this trigger signal will be referred to as an "inattention trigger") to the warning controlling ECU 110A for each determination cycle in which it has been determined that the driver is not facing forward.

The driver monitoring ECU 210 also detects whether the eyes of the driver are closed based on the opening amount of the eyelids of the driver (i.e., the eyelid opening amount) by processing the face image that is input as needed from the driver monitor camera 212. There are a multitude of various methods for detecting whether the eyes of the driver are closed based on image processing. Any appropriate method may be used. For example, face orientation and size in the face image may be corrected by affine transformation or the like, and then after edge processing, the parts of the face may be specified by matching the parts of the face (i.e., mouth, nose, eyes). Next, the maximum distance between the upper and lower eyelids (i.e., the eyelid opening amount) is obtained based on the characteristic amount of the eyes, i.e., based on a string of coordinates of a boundary line of the eyelids in this example embodiment. When the eyelid opening amount is equal to or less than a predetermined reference value, it is determined that the eyes of the driver are closed. The predetermined value in this case may be a value suitable for each driver. That is, the predetermined reference value is derived in advance by sensory evaluation (i.e., by measuring both the opening amount of the eyelids when the eyes of each driver are open and the opening amount of the eyelids when the eyes of each driver are closed), and making a database for each driver. The driver monitoring ECU 210 makes the foregoing determination for each image frame or for each set of a determined number of continuous image frames and supplies the determination results to the warning controlling ECU 110A for each determination cycle. In this example, the driver monitoring ECU 210 supplies a trigger signal indicating that the eyes of the driver are closed (hereinafter this trigger signal will be referred to as a "closed-eye trigger") to the warning controlling ECU 110A for each determination cycle in which it has been determined that the eyes of the driver are closed.

The inattention trigger counting portion 112 of the warning controlling ECU 110A measures the duration of the inattentive state of the driver based on the inattention trigger input from the driver monitoring ECU 210. More specifically, the inattention trigger counting portion 112 increases an inattention counter value (the initial value of which is zero) incrementally when an inattention trigger is input in a given determination cycle, and increases the inattention counter value incrementally every time an inattention trigger is input in a determination cycle thereafter. The inattention trigger counting portion 112 basically counts the inattention triggers that are input in consecutive determination cycles. However, a filter may also be used that retains the inattention trigger value even when the inattention triggers are momentarily interrupted. The inattention counter value corresponds to the duration of the inattentive state of the driver, i.e., the inattentive time.

The inattention warning necessity determining portion 114 of the warning controlling ECU 110A determines whether the current inattentive time has exceeded a first predetermined period of time Ta [ms] in every determination cycle that is synchronized with the determination cycle of the driver monitoring ECU 210. More specifically, the inattention warning necessity determining portion 114 determines whether the inattention counter value has exceeded a first predetermined threshold value corresponding to the first predetermined period of time Ta every time the inattention counter value is incrementally increased. When the inattention counter value has exceeded the first predetermined threshold value, the inattention warning necessity determining portion 114 determines that an inattention warning is necessary and outputs an inattention warning command to the warning ECU 230. Other conditions (excluding a condition related to the closed-eye time which will be described later) may also be added as conditions for outputting the inattention warning command. For example, a condition that the vehicle speed be equal to or greater than a predetermined value based on the wheel-side sensor 270 and a condition that the vehicle behavior be unstable based on image recognition results of the lane boundary line from the white line detecting ECU 290 or the output value from the steering sensor 274 or the like (e.g., when the vehicle is wandering in such a way that it intermittently crosses the lane boundary line) may also be used as AND conditions for outputting the inattention warning command.

The warning ECU 230 outputs an inattention warning via the buzzer 240 in response to the inattention warning command from the inattention warning necessity determining portion 114 of the warning controlling ECU 110A. The mode in which the inattention warning is output is not limited to audio. For example, a vibrating body embedded in the seat or steering wheel may be made to vibrate, the driver may be thermally stimulated by temperature changing means (such as a heater or a Peltier element) embedded in the seat or steering wheel, a large amount of air may suddenly be blown from an air-conditioner outlet, the driver may be alerted by a light being automatically shined at him or her, or the driver may be alerted by the brake ECU 250 forcibly braking the vehicle by driving the brake actuator 260.

The closed-eye trigger counting portion 116 of the warning controlling ECU 110A measures the duration of the dozing state of the driver based on the closed-eye trigger input from the driver monitoring ECU 210. More specifically, the closed-eye trigger counting portion 116 increases a closed-eye counter value (the initial value of which is zero) incrementally when a closed-eye trigger is input in a given determination cycle, and increases the closed-eye counter value incrementally every time a closed-eye trigger is input in a determination cycle thereafter. The closed-eye trigger counting portion 116 basically counts the closed-eye triggers that are input in consecutive determination cycles. However, a filter may also be used that retains the closed-eye trigger value even when the inattention triggers are momentarily interrupted. The closed-eye counter value corresponds to the duration of the closed-eye state of the driver, i.e., the closed-eye time.

The dozing warning necessity determining portion 118 of the warning controlling ECU 110A determines whether the current closed-eye time has exceeded a second predetermined period of time Tb [ms] in every determination cycle that is synchronized with the determination cycle of the driver monitoring ECU 210. More specifically, the dozing warning necessity determining portion 118 determines whether the closed-eye counter value has exceeded a second predetermined threshold value corresponding to the second predetermined period of time Tb every time the closed-eye counter value is incrementally increased by the closed-eye trigger counting portion 116. When the closed-eye counter value has exceeded the second predetermined threshold value, the dozing warning necessity determining portion 118 determines that a dozing warning is necessary and outputs a dozing warning command to the warning ECU 230. Similar to the condition for outputting the inattentive warning command, other conditions (excluding a condition related to the inattentive time described above) may also be added as conditions for outputting the dozing warning command.

The warning ECU 230 outputs a dozing warning via the buzzer 240 in response to the dozing warning command from the dozing warning necessity determining portion 118 of the warning controlling ECU 110A. Like the mode in which the inattention warning is output, the mode in which the dozing warning is output is not limited to audio. Also, the mode in which the dozing warning is output may be the same as the mode in which the inattention warning is output or different than that mode. When it is the same, the warning command output from the warning controlling ECU 110A may be the same signal.

Here, in this example embodiment, it will be assumed that when the driver is inattentive, his or her reaction to a warning will be slower than it is when the driver is dozing off because when the driver is inattentive, he or she is concentrating on something in a direction other than straight ahead. Therefore, the first predetermined period of time Ta which is the threshold value for the inattentive time described above is set shorter than the second period of time Tb which is the threshold value for the closed-eye time. Accordingly, the warning is issued earlier when the driver is inattentive because the first predetermined period of time Ta is set shorter than the second predetermined period of time Tb. The first predetermined period of time Ta may be set longer than, for example, the time required for the driver to make a safety check or check a display on a navigation device. Also, the second predetermined period of time Tb may be set longer than the period of time after the eyes of the driver close until the level of consciousness (level of alertness) drops and the driver starts to doze off. Alternatively, the second predetermined period of time Tb may be set longer than the normal blinking duration but shorter than the time after the time the eyes of the driver close until the driver falls completely asleep. That is, the second predetermined period of time Tb may also be set to a period during which it could be said that the driver is not asleep.

Figure 2:
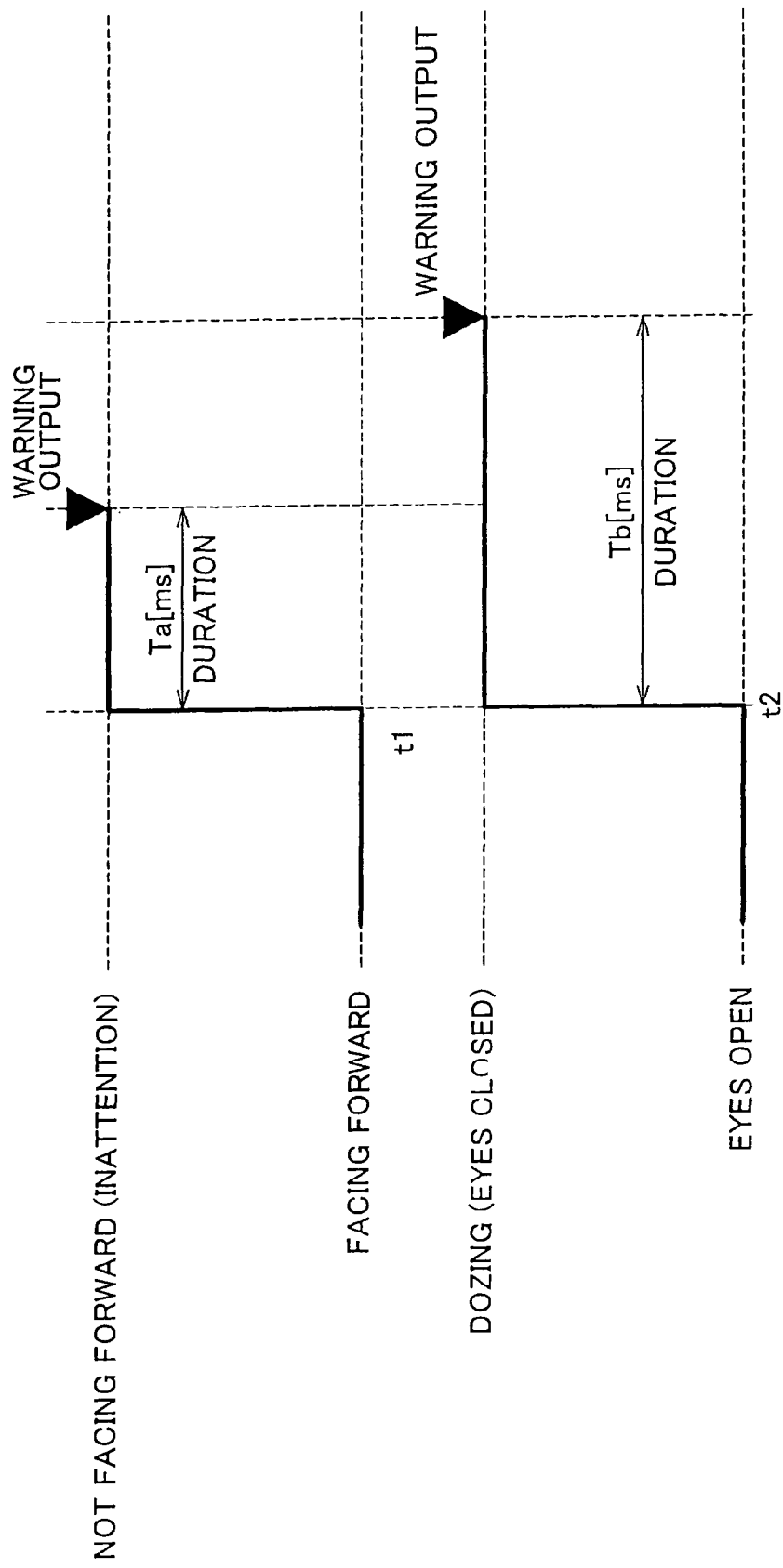
FIG. 2 is a timing chart schematically showing the difference between a second predetermined time Tb and a first predetermined time Ta.

FIG. 2 is a timing chart schematically showing the difference between the second predetermined period of time Tb and the first predetermined period of time Ta. In FIG. 2, the horizontal axis represents time and the vertical axis represents the output states of the inattention trigger and the closed-eye trigger. In the example shown in FIG. 2, the inattention trigger indicating that an inattentive state is being detected is output continuously from time t1. Also, closed-eye trigger (which is equivalent to the dozing trigger in this embodiment) indicating that a dozing state is being detected is continuously output from time t2. Incidentally, time t1 and time t2 in FIG. 2 are both at the same position on the time line for the sake of convenience in order to make it easier to compare the lengths of the second predetermined period of time Tb and the first predetermined period of time Ta.

In this example embodiment, as described above, different threshold values (i.e., the second predetermined period of time Th and the first predetermined period of time Ta) are set for the inattentive time and the dozing time. Moreover, the first predetermined period of time Ta is set shorter than the second predetermined period of time Tb according to the respective characteristics of the inattentive state and the dozing state. Accordingly, as shown in FIG. 2, for example, the period of time from the time when the inattentive state starts to be detected until the inattention warning is output is shorter than the period of time from the time when the dozing state starts to be detected until the dozing warning is output. That is, a warning is output earlier for the inattentive state than it is for the dozing state.

In this way, according to this example embodiment, as described above the first predetermined period of time Ta is set shorter than the second predetermined period of time Tb so warnings can be output at timings appropriate for the respective characteristics of the inattentive state and the dozing state. That is, a warning is output earlier for an inattentive state, for which characteristically the response to a warning is relatively slow, than it is for a dozing state, for which the response to a warning is thought to be relatively fast. As a result, the warning is more useful so the safety of the driver can be ensured.

Second Example Embodiment

Next, a second example embodiment of the invention will be described. In the first example embodiment, the first predetermined period of time Ta that serves as the threshold value for the inattentive time is set shorter than the second predetermined period of time Tb that serves as the threshold value for the closed-eye time. However, in the second example embodiment, it will be assumed that when the driver is dozing off, it takes time for him or her to become alert so the second predetermined period of time Tb that serves as the threshold value for the closed-eye time described above is set shorter than the first predetermined period of time Ta that serves as the threshold value for the inattentive time. That is, when the driver is dozing off, his or her reaction to the warning tends to be slower than when he or she is inattentive in which case it requires no time to become alert. Therefore, it is useful to issue the warning that much earlier. The first predetermined period of time Ta may be set longer than, for example, the amount of time that it takes for the driver to make a safety check or check a display on a navigation device. Also, the second predetermined period of time Th may be set longer than the duration of a normal blink in order to prevent unnecessary warnings from being issued frequently due to blinking. For example, the second the second predetermined period of time Tb may be set longer than the normal blinking duration but shorter than the time after the time the eyes of the driver close until the driver falls completely asleep. That is, the second predetermined period of time Tb may also be set to a period during which it could be said that the driver is not asleep. This is because even if the driver's eyes are closed not for a duration for which it could be said that he or she is asleep, the pupils will become larger when the eyes close so it is difficult for the driver to recognize objects outside until the pupils adjust to the light outside when the eyes open. It is therefore useful to issue a warning earlier when the driver is dozing than when the driver is inattentive in which case there is no such delay in recognition.

Figure 3:
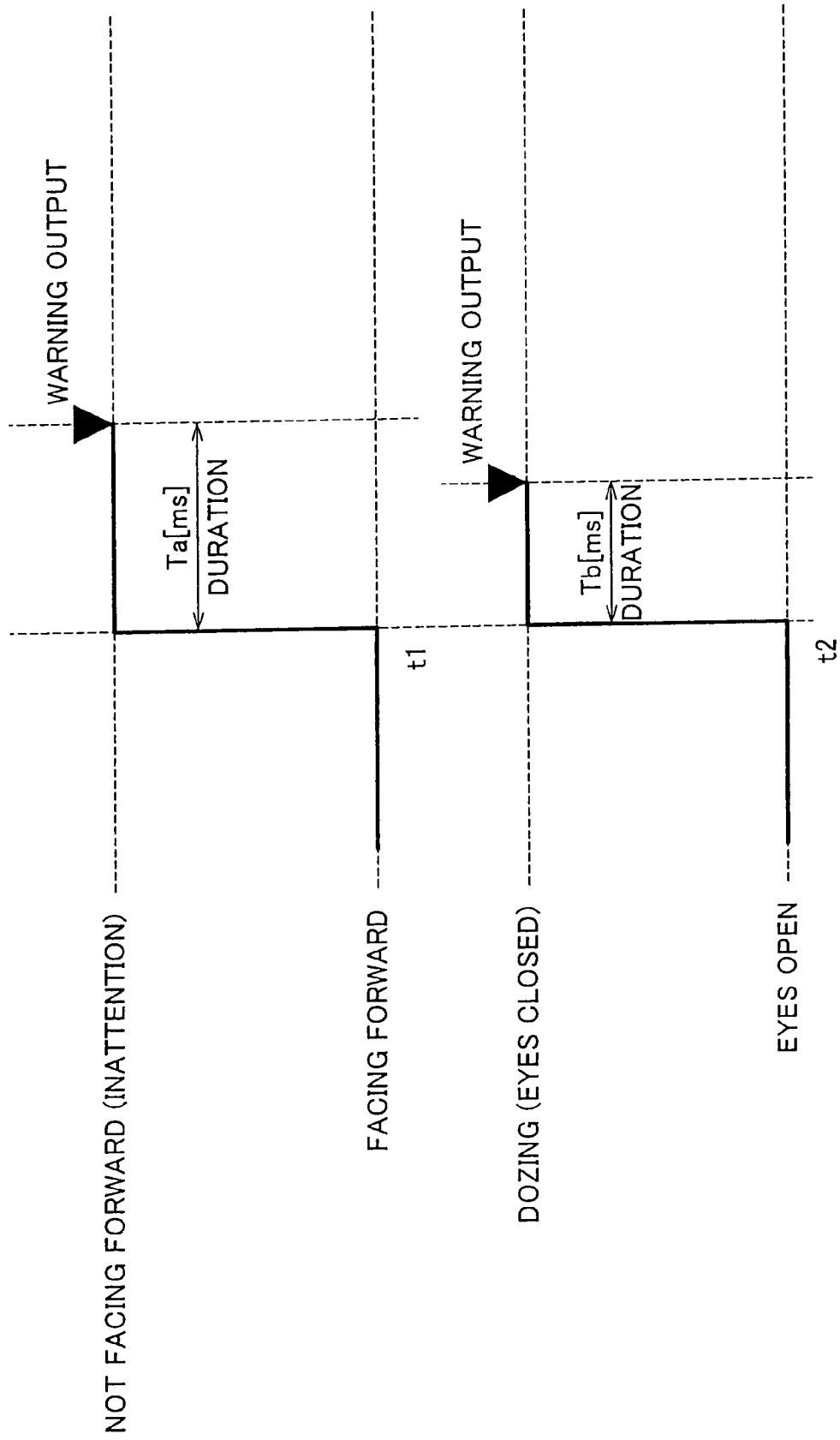
FIG. 3 is a timing chart schematically showing the difference between the second predetermined time Tb and the first predetermined time Ta according to a second example embodiment of the invention.

FIG. 3 is a timing chart schematically showing the difference between the second predetermined period of time Tb and the first predetermined period of time Ta according to the second example embodiment of the invention. In FIG. 3, the horizontal axis represents time and the vertical axis represents the output states of the inattention trigger and the closed-eye trigger. In the example shown in FIG. 3, the inattention trigger indicating that an inattentive state is being detected is output continuously from time t1. Also, closed-eye trigger (which is the dozing trigger in this embodiment) indicating that a dozing state is being detected is continuously output from time t2. Incidentally, time t1 and time t2 in FIG. 3 are both at the same position on the time line for the sake of convenience in order to make it easier to compare the lengths of the second predetermined period of time Tb and the first predetermined period of time Ta.

In this example embodiment, as described above, different threshold values (i.e., the second predetermined period of time Tb and the first predetermined period of time Ta) are set for the inattentive time and the dozing time. Moreover, the second predetermined period of time Tb is set shorter than the first predetermined period of time Ta according to the respective characteristics of the inattentive state and the dozing state. Accordingly, as shown in FIG. 3, for example, the period of time from the time when the dozing state starts to be detected until the dozing warning is output is shorter than the period of time from the time when the inattentive state starts to be detected until the inattention warning is output. That is, the warning is output sooner for the dozing state than it is for the inattentive state.

In this way, according to this example embodiment, as described above the second predetermined period of time Tb is set shorter than the first predetermined period of time Ta so warnings can be output at timings appropriate for the respective characteristics of the inattentive state and the dozing state. That is, a warning is output earlier for a dozing state, for which characteristically the response to a warning is relatively slow, than it is for an inattentive state, for which the response to a warning is thought to be relatively fast. As a result, the warning is issued at a timing when the warning is significant so the safety of the driver can be ensured.

Incidentally, in the first and second example embodiments, the inattentive time measuring device of the invention can be regarded as being cooperatively realized by the driver monitor camera 212, the driver monitoring ECU 210, and the inattention trigger counting portion 112 of the warning controlling ECU 110A. Also, the dozing time measuring device or the closed-eye time measuring device of the invention can be regarded as being cooperatively realized by the driver monitor camera 212, the driver monitoring ECU 210, and the closed-eye trigger counting portion 116 of the warning controlling ECU 110A. The first warning output device of the invention can be regarded as being cooperatively realized by the inattention warning necessity determining portion 114 of the warning controlling ECU 110A, the warning ECU 230, and the buzzer 240. The second warning output device of the invention can be regarded as being cooperatively realized by the dozing warning necessity determining portion 118 of the warning controlling ECU 110A, the warning ECU 230, and the buzzer 240.

The first and second example embodiments described above may also be modified as follows.

For example, in the foregoing example embodiment, the duration of the closed-eye state of the driver (i.e., the closed-eye time) is measured as the duration of the dozing state of the driver (i.e., the dozing time). However, the dozing time may be measured using another parameter instead of, or in addition to, the time that the eyes of the driver are closed. For example, the dozing time may also be measured using various physiological characteristic amounts such as brain waves, magneto encephalography, heartbeat or fluctuation in heartbeat, or body surface temperature of the driver or the manner of change in the body surface temperature of the driver. In this case, the same effects that are obtained with the foregoing first example embodiment can also be obtained by setting the threshold value for the duration of the inattentive state, i.e., the first predetermined period of time Ta, shorter than the second predetermined period of time Tb as it is in the first example embodiment. Also, the same effects that are obtained with the foregoing second example embodiment can also be obtained by setting the threshold value for the duration of the dozing state, i.e., the second predetermined period of time Tb, shorter than the first predetermined period of time Ta as it is in the second example embodiment.

Third Example Embodiment

Figure 4:
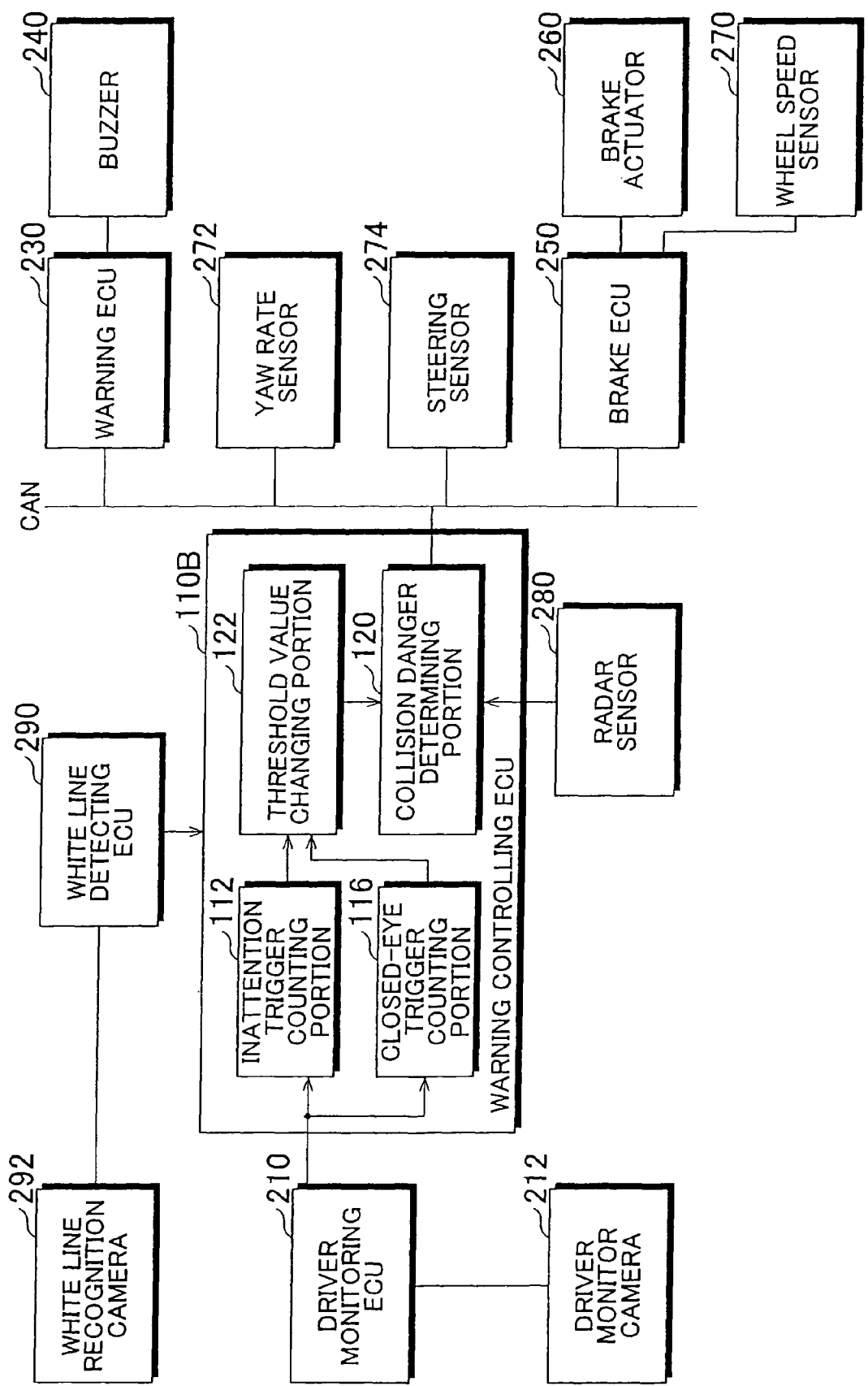
FIG. 4 is a system block diagram which shows an example of the main structure of a warning system that includes an on-board warning apparatus according to a third example embodiment of the invention.

FIG. 4 is a system block diagram which shows an example of the main structure of a warning system that includes an on-board warning apparatus according to a third example embodiment of the invention. The constituent elements denoted by the same reference numerals as in the first example embodiment described above may be the same as those in the foregoing first example embodiment unless specifically mentioned. The third example embodiment illustrates a case in which it is assumed that there is a tendency for it to take longer for the driver to respond to a warning when he or she is inattentive than it does when he or she is dozing off because when the driver is inattentive, he or she is not facing forward.

A warning controlling ECU 110B is provided with function blocks that realize main functions. These function blocks include an inattention trigger counting portion 112, a closed-eye trigger counting portion 116, a collision danger determining portion 120, and a threshold value changing portion 122.

The collision danger determining portion 120 determines whether there is a danger of collision between the host vehicle and an object in front of the host vehicle by monitoring the relative relationship between the host vehicle and an object in front of the host vehicle based on information about the object in front of the host vehicle that is supplied each predetermined cycle from the radar sensor 280. In this example, the collision danger determining portion 120 calculates/monitors the time between the host vehicle and the object in front of the host vehicle based on the information from the radar sensor 280 regarding the object in front of the host vehicle at each predetermined cycle. When the calculated vehicle-to-object time falls below a predetermined threshold value Th, the collision danger determining portion 120 determines that there is a danger of collision between the host vehicle and the object in front of the host vehicle. Here, the vehicle-to-object time is the time from the current point to the point at which it is estimated that the host vehicle will collide with the object in front of the host vehicle. More simply, the vehicle-to-object time may be calculated by dividing the distance between the host vehicle and the object in front of the host vehicle by the relative speed of the host vehicle and the object in front of the host vehicle. The predetermined threshold value Th can be a default value T0 as long as the inattention trigger or the closed-eye trigger (which is the dozing trigger in this embodiment) is not being output, as will be described later. The default value T0 is preferably set to within a period (time range) when the warning output is significant at a time well before collision is estimated to occur. Further, the default value T0 may be longer than the time between the point at which a collision becomes unavoidable and the estimated time of collision, for example. The structure is preferably such that collision avoidance steering is performed by an automatic steering mechanism, not shown, and forced emergency braking by the brake ECU 250 when it is determined that a collision is unavoidable. The reason for setting the default time T0 longer than the time between the point at which a collision becomes unavoidable and the estimated time of collision is because even if the driver is alerted of an unavoidable collision by the warning, any operation performed by the driver himself or herself to avoid the collision is meaningless so there is little sense in issuing a warning once a collision is unavoidable. However, the default value T0 may also be a time corresponding to the collision unavoidable state.

Incidentally, other conditions may be added to the condition for determining whether there is a danger of collision. Examples of other conditions include a condition that the angle created by a speed vector between the host vehicle and the object in front of the host vehicle be within a predetermined angle and a condition that the speed of the host vehicle be equal to or greater than a predetermined value.

When the collision danger determining portion 120 determines that there is a danger of collision, it outputs a collision danger warning command to the warning ECU 230 to issue a collision danger warning.

The warning ECU 230 outputs a collision danger warning command via the buzzer 240 in response to the collision danger warning command from the collision danger determining portion 120 of the warning controlling ECU 110B. Incidentally, the mode in which the inattention warning is output is not limited to audio. For example, a vibrating body embedded in the seat or steering wheel may be made to vibrate, the driver may be thermally stimulated by temperature changing means (such as a heater or a Peltier element) embedded in the seat or steering wheel, a large amount of air may suddenly be blown from an air-conditioner outlet, the driver may be alerted by a light being automatically shined at him or her, or the driver may be alerted by the brake ECU 250 forcibly braking the vehicle by driving the brake actuator 260.

The threshold value changing portion 122 changes, according to the current inattentive time and closed-eye time, the predetermined threshold value Th from the default value T0 to a value that makes the collision danger determining portion 120 more sensitive to determining a danger of collision (i.e., such that the collision danger determining portion 120 more readily determines that there is a danger of collision). More specifically, the threshold value changing portion 122 increases the predetermined threshold value Th by an amount corresponding to the inattention trigger counting value and the closed-eye trigger counting value at the current time.

Accordingly, in this example embodiment, if the driver is currently inattentive or dozing off, the predetermined threshold value Th is increased according to the inattentive time or closed-eye time so the timing at which the vehicle-to-object time falls below the predetermined threshold value Th is advanced (i.e., the warning is issued earlier) by a corresponding amount. That is, the timing at which the warning is issued is advanced so a so-called advanced warning can be realized.

FIG. 5A is a graph showing the manner of change in the predetermined threshold value Th according to the inattentive time, while FIG. 5B is a graphs showing the manner of change in the predetermined threshold value Th according to the closed-eye time. The horizontal axis in FIG. 5A represents the inattentive time, while the horizontal axis in FIG. 5B represents the closed-eye time. The vertical axis in both FIG. 5A and FIG. 5B represents the predetermined threshold value Th.

As shown in FIG. 5A, the predetermined threshold value Th increases toward an upper limit value Tx as the inattentive time increases. In the example in the drawing, when the inattentive time becomes Ta [ms], the predetermined threshold value Th reaches the upper limit value Tx and is maintained there even if the inattentive time becomes greater than Ta. Also, until the inattentive time reaches Ta, the predetermined threshold value Th increases non-linearly in a convex curve that arcs upward, as shown in FIG. 5A. Incidentally, the value of the inattentive time Ta can be set just as it is in the first example embodiment described above.

As shown in FIG. 5B, the predetermined threshold value Th increases towards an upper limit value Ty as the closed-eye time increases. In the example in the drawing, when the closed-eye time becomes Tb [ms], the predetermined threshold value Th reaches the upper limit value Ty and is maintained there even if the closed-eye time becomes greater than Tb. Also, until the closed-eye time reaches Tb, the predetermined threshold value Th increases non-linearly in a concave curve that arcs downward, as shown in FIG. 5B. Incidentally, the value of the closed-eye time Tb can be set just as it is in the first example embodiment described above, in which it is greater than the inattentive time Ta (i.e., Tb>Ta).

Here, the upper limit value Ty is set to a smaller value than the upper limit value Tx. This is because there is a tendency for it to take longer for the driver to respond to a warning when he or she is inattentive than when he or she is dozing off given the characteristics of inattentiveness and dozing.

Accordingly, in this example embodiment, the collision danger determining portion 120 more readily determines that there is a danger of collision when the inattentive state is detected than when the dozing state is detected. Therefore, the output timing of the warning is earlier when the inattentive state is detected than it is when the dozing state is detected.

In this way, according to this example embodiment, the warning can be output at an appropriate timing according to the difference in characteristics of the dozing state and the inattentive state by focusing on the difference in the characteristics of the dozing state and the inattentive state and advancing the timing of the warning output differently for the dozing state than for the inattentive state. That is, there is a tendency for it to take longer for the driver to respond to a warning when he or she is inattentive than when he or she is dozing off because when the driver is inattentive, he or she is not facing forward. Accordingly, a warning when the driver is inattentive can be output a corresponding amount of time earlier.

Also in this example embodiment, even if the current inattentive time is less than time Ta or if the current closed-eye time is less than time Tb, i.e., even if the predetermined threshold value Th for the inattentive time is less than the upper limit value Tx or if the predetermined threshold value Th for the closed-eye time is less than the upper limit value Ty, the warning is output at an earlier timing. This is because even in these situations it is very likely that the driver is not paying sufficient attention to the area in front of the vehicle so it is effective to advance the warning timings slightly.

Here, as is evident by comparing FIG. 5A and FIG. 5B, in this example embodiment, the amount of change in the predetermined threshold value Th for inattentive time is greater than the amount of change in the predetermined threshold value Th for the closed-eye time over the entire region from 0 to Tb on the horizontal axis. This is achieved i) by making the upper limit value Tx greater than the upper limit value Ty, and ii) because of the difference in the direction in which the curve protrudes, as described above. According to this structure, the amount the warning is advanced for the inattentive state is made larger than the amount the warning is advanced for the dozing state according to the difference in the characteristics of the dozing state and the inattentive state. Thus, the warning timing can be advanced appropriately depending on the characteristics of the respective states.

The third example embodiment described above may also be modified as follows.

In the third example embodiment, the change curve of the predetermined threshold value Th for the inattentive state curves upward (i.e., is convex) until the upper limit value Tx and the change curve of the predetermined threshold value Th for the dozing state curves downward (i.e., is concave) until the upper limit value Ty. Alternatively, however, only one of these may be realized. For example, only the change curve of the predetermined threshold value Th for the inattentive state may be curved upward (i.e., convex), while the change curve of the predetermined threshold value Th for the dozing state may be a straight line. Conversely, only the change curve of the predetermined threshold value Th for the dozing state may be curved downward (i.e., concave), while the change curve of the predetermined threshold value Th for the inattentive state may be a straight line. Alternatively, the upper limit value Tx may simply be made greater than the upper limit value Ty (i.e., the characteristic of the change in the predetermined threshold values Th for the inattentive state and the dozing state may be linear for both).

Also, the third example embodiment described above can also be combined with the foregoing first example embodiment. In this case, with respect to inattentiveness, for example, when the inattentive time is less than Ta, a collision danger warning can be output if it is determined that there is a danger of collision. When the inattentive time becomes equal to or greater than Ta, an inattention warning is output. However, if it is determined that there is a danger of collision and the inattentive time is equal to or greater than Ta, a collision danger warning, in addition to an inattention warning, may also be output. This structure is especially preferably when the output mode of a collision danger warning differs from the output mode of an inattention warning.

Fourth Example Embodiment

Next, a fourth example embodiment of the invention will be described. The fourth example embodiment illustrates a case in which it is assumed that there is a tendency for it to take longer for the driver to become aware of the area in front of the vehicle when he or she is dozing off, i.e., in a state of low awareness, than when he or she is inattentive due to the characteristics of dozing and inattentiveness. FIG. 6A is a graph showing the manner of change in the predetermined threshold value Th according to the inattentive time and FIG. 6B is a graph showing the manner of change in the predetermined threshold value Th according to the closed-eye time. The horizontal axis in FIG. 6A represents the inattentive time, while the horizontal axis in FIG. 6B represents the closed-eye time. The vertical axis in both FIG. 6A and FIG. 6B represents the predetermined threshold value Th.

As shown in FIG. 6A, the predetermined threshold value Th increases toward the upper limit value Tx as the inattentive time increases. In the example in the drawing, when the inattentive time becomes Ta [ms], the predetermined threshold value Th reaches the upper limit value Tx and is maintained there even if the inattentive time becomes greater than Ta. Also, until the inattentive time reaches Ta, the predetermined threshold value Th increases non-linearly in a concave curve that arcs downward, as shown in FIG. 6A. Incidentally, the value of the inattentive time Ta can be set just as it is in the second example embodiment described above. The upper limit value Tx is the time that it takes for the driver to face forward from an inattentive state when prompted by a warning, and become aware of the area in front of the vehicle.

As shown in FIG. 6B, the predetermined threshold value Th increases towards an upper limit value Ty as the closed-eye time increases. In the example in the drawing, when the closed-eye time becomes Tb [ms], the predetermined threshold value Th reaches the upper limit value Ty and is maintained there even if the closed-eye time becomes greater than Tb. Also, until the-closed-eye time reaches Tb, the predetermined threshold value Th increases non-linearly in a convex curve that arcs upward, as shown in FIG. 6B. Incidentally, the value of the closed-eye time Tb can be set just as it is in the second example embodiment described above, in which it is equal to or less than the inattentive time Ta (i.e., Tb≦Ta). The upper limit value Ty is the time that it takes for the driver to awaken from a dozing state (a closed-eye state in this example), open his or her eyes when prompted by a warning, and become aware of the area in front of the vehicle. Here, the upper limit value Ty is set to a value larger than the upper limit value Tx. This is because there is a tendency for it to take longer for the driver to respond to a warning when he or she is dozing off, i.e., in a state of low awareness, than when he or she is inattentive given the characteristics of dozing and inattentiveness.

Accordingly, in this example embodiment, the collision danger determining portion 120 more readily determines that there is a danger of collision when the dozing state is detected than when the inattentive state is detected. Therefore, the output timing of the warning is earlier when the dozing state is detected than when the inattentive state is detected.

In this way, according to this example embodiment, the warning can be output at an appropriate timing according to the difference in characteristics of the dozing state and the inattentive state by focusing on the difference in the characteristics of the dozing state and the inattentive state and advancing the timing of the warning output differently for the dozing state than for the inattentive state. That is, there is a tendency for it to take longer for the driver to respond to the warning when he or she is dozing off, i.e., in a state of low awareness, than when he or she is inattentive due to the characteristics of dozing and inattentiveness. Accordingly, a warning when the driver is dozing off can be output a corresponding amount of time earlier.

Also in this example embodiment, even if the current inattentive time is less than time Ta or if the current closed-eye time is less than time Tb, the warning is output at an earlier timing regardless of whether the predetermined threshold value Th for the inattentive time is less than the upper limit value Tx or the predetermined threshold value Th for the closed-eye time is less than the upper limit value Ty. This is because even in these situations it is very likely that the driver is not paying sufficient attention to the area in front of the vehicle so it is effective to advance the warning timings slightly.

Here, as is evident with comparing FIG. 6A and FIG. 6B, in this example embodiment, the amount of change in the predetermined threshold value Th for the inattentive time is greater than the amount of change in the predetermined threshold value Th for the dozing time over the entire region from 0 to Tb on the horizontal axis. This is achieved i) by making the upper limit value Ty greater than the upper limit value Tx, and ii) because of the difference in the direction in which the curve protrudes, as described above. According to this structure, the amount the warning is advanced for the dozing state is made larger than it is for the inattentive state according to the difference in the characteristics of the dozing state and the inattentive state. Thus, the warning timing can be advanced appropriately depending on the characteristics of the respective states.

The fourth example embodiment described above may also be modified as follows.

In the foregoing example embodiment, the closed-eye time is measured as the dozing time. Alternatively, however, the dozing time may be measured using another parameter instead or in addition to the eyes of the driver being closed. For example, the dozing time may be measured using various physiological characteristic amounts such as brain waves. In this case as well, similar effects as those obtained in the foregoing example embodiment can be obtained by setting the increase amount of the predetermined threshold value Th for the duration of the dozing state larger than the increase amount of the predetermined threshold value Th for the duration of the inattentive state.

Also, in the foregoing example embodiment, the change curve of the predetermined threshold value Th for the inattentive state curves downward (i.e., is concave) until the upper limit value Tx and the change curve of the predetermined threshold value Th for the dozing state curves upward (i.e., is convex) until the upper limit value Ty. Alternatively, however, only one of these may be realized. For example, only the change curve of the predetermined threshold value Th for the inattentive state may be curved downward (i.e., concave), while the change curve of the predetermined threshold value Th for the dozing state may be a straight line. Conversely, only the change curve of the predetermined threshold value Th for the dozing state may be curved upward (i.e., convex), while the change curve of the predetermined threshold value Th for the inattentive state may be a straight line. Alternatively, the upper limit value Ty may simply be made greater than the upper limit value Tx (i.e., the characteristic of the change in the predetermined threshold values Th for the inattentive state and the dozing state may be linear for both).

Also, the fourth example embodiment described above can also be combined with the foregoing second example embodiment. In this case, with respect to inattentiveness, for example, when the inattentive time is less than Ta, a collision danger warning can be output if it is determined that there is a danger of collision. When the inattentive time becomes equal to or greater than Ta, an inattention warning is output. However, if it is determined that there is a danger of collision and the inattentive time is equal to or greater than Ta, a collision danger warning, in addition to an inattention warning, may also be output. This structure is especially preferably when the output mode of a collision danger warning differs from the output mode of an inattention warning.

Also, the third and fourth example embodiment may also be modified as follows. For example, in the foregoing example embodiment, whether or not there is a danger of collision is determined based on the vehicle-to-object time and the predetermined threshold value Th. However, this determination may also be made by another method. For example, a two-dimensional map may be used which is defined by the distance between the host vehicle and the object in front of the host vehicle, and the relative speed of the host vehicle and the object in front of the host vehicle. In this case, when the threshold value curve divides the two-dimensional map into a danger-of-collision region and a no-danger-of-collision region, for example, and the current vehicle-to-object distance and relative speed are in the danger-of-collision region as defined by the threshold value curve, it may be determined that there is a danger of collision danger. Also, whether or not there is a danger of collision may also be determined using another physical quantity other than the vehicle-to-object distance and relative speed, such as acceleration (or deceleration).

Also, in the foregoing example embodiment, information indicative of the relative relationship between the host vehicle and the object in front of the host vehicle is obtained by the radar sensor 280. However, the same information may also be obtained using an image sensor instead of, or in addition to, the radar sensor 280. When the host vehicle is provided with communication equipment capable of two-way communication with the object in front of the vehicle, the same information may also be obtained via that communication (such as vehicle-to-vehicle communication).

In the third and fourth example embodiments, the collision danger determining device of the invention can be regarded as being cooperatively realized by the radar sensor 280 and the collision danger determining portion 120 of the warning controlling ECU 110B. Also, the warning outputting device of the invention can be regarded as being cooperatively realized by the collision danger determining portion 120 of the warning controlling ECU 110B, the warning ECU 230, and the buzzer 240. The inattentive time measuring device of the invention can be regarded as being cooperatively realized by the driver monitor camera 212, the driver monitoring ECU 210, and the inattention trigger counting portion 112 of the warning controlling ECU 110B. The dozing time measuring device or the closed-eye time measuring device of the invention can be regarded as being cooperatively realized by the driver monitor camera 212, the driver monitoring ECU 210, and the closed-eye trigger counting portion 116 of the warning controlling ECU 110B. Further, the threshold value changing device of the invention can be regarded as being realize by the threshold value changing portion 122 of the warning controlling ECU 110B.

While the invention has been described with reference to example embodiments thereof, it is to be understood that the invention is not limited to these example embodiments but may be embodied with various changes or modifications without departing from the spirit and scope of the invention.

The invention claimed is:

1. An on-board warning apparatus comprising:
   an inattentive time measuring device that measures a duration of an inattentive state of a driver;
   a dozing time measuring device that measures a duration of a dozing state of the driver;
   a first warning output device that warns the driver when the measured inattentive time exceeds a first predetermined period of time; and
   a second warning output device that warns the driver when the measured dozing time exceeds a second predetermined period of time,
   wherein the first predetermined time is shorter than the second predetermined period of time, and
   wherein the on-board warning device is configured such that the duration of the inattentive state from the time when the inattentive time measuring device starts to detect the inattentive state until the first warning output device starts to warn the driver by outputting an inattentive warning is shorter than the duration of the dozing state from the time when the dozing time measuring device starts to detect the dozing state until the second warning output device starts to warn the driver by outputting a dozing warning.

2. An on-board warning apparatus comprising:
   a collision danger determining device that determines whether there is a danger of collision between a host vehicle and an object in front of the host vehicle based on a relationship between a predetermined threshold value and a physical quantity capable of indicating a relative relationship between the host vehicle and the object in front of the host vehicle;
   a warning output device that warns a driver when the collision danger determining device determines that there is a danger of collision;
   an inattentive time measuring device that measures a duration of an inattentive state of the driver;
   a dozing time measuring device that measures a duration of a dozing state of the driver; and
   a threshold value changing device that changes the predetermined threshold value according to one of the measured inattentive time and the dozing time so that the collision danger determining device more readily determines that there is a danger of collision,
   wherein an amount of change in the predetermined threshold value for the inattentive time is greater than an amount of change in the predetermined threshold value for the dozing time.

3. The on-board warning apparatus according to claim 1, wherein the dozing time measuring device measures a duration of a state in which the eyes of the driver are closed as the dozing time.

4. An on-board warning apparatus comprising:
   an inattentive time measuring device that measures a duration of an inattentive state of a driver;
   a closed-eye time measuring device that measures a time during which the eyes of the driver are closed;
   a first warning output device that warns the driver when the measured inattentive time exceeds a first predetermined period of time; and
   a second warning output device that warns the driver when the measured closed-eye time exceeds a second predetermined period of time,
   wherein the first predetermined time is shorter than the second predetermined period of time, and
   wherein the on-board warning device is configured such that the duration of the inattentive state from the time when the inattentive time measuring device starts to detect the inattentive state until the first warning output device starts to warn the driver by outputting an inattentive warning is shorter than the duration of the dozing state from the time when the dozing time measuring device starts to detect the dozing state until the second warning output device starts to warn the driver by outputting a dozing warning.

5. An on-board warning apparatus comprising:
   a collision danger determining device that determines whether there is a danger of collision between a host vehicle and an object in front of the host vehicle based on a relationship between a predetermined threshold value and a physical quantity capable of indicating a relative relationship between the host vehicle and the object in front of the host vehicle;
a warning output device that warns a driver when the collision danger determining device determines that there is a danger of collision;
an inattentive time measuring device that measures a duration of an inattentive state of the driver;
a closed-eye time measuring device that measures a time during which the eyes of the driver are closed; and
a threshold value changing device that changes the predetermined threshold value according to one of the measured inattentive time and the closed-eye time so that the collision danger determining device more readily determines that there is a danger of collision,
wherein an amount of change in the predetermined threshold value for the inattentive time is greater than an amount of change in the predetermined threshold value for the closed-eye time.

6. The on-board warning apparatus according to claim 1, wherein the inattentive time measuring device measures a duration of a state in which the driver is not facing forward as the inattentive time.

7. An on-board warning apparatus comprising:
a first detection device that detects an inattentive state of a driver;
a second detection device that detects at least one of a dozing state of the driver and a state in which the eyes of the driver are closed;
a first measuring device that measures a duration of the inattentive state of the driver;
a second measuring device that measures at least one of a duration of the dozing state of the driver and a time during which the eyes of the driver are closed; and
a warning device that issues a warning to the driver,
wherein the period of time from the time that the inattentive state is detected until time that the warning is issued is shorter than the period of time from the time that at least one of the dozing state of the driver and the state in which the eyes of the driver are closed is detected until the time that the warning is issued, and
wherein the on-board warning device is configured such that the duration of the inattentive state from the time when the inattentive time measuring device starts to detect the inattentive state until the first warning output device starts to warn the driver by outputting an inattentive warning is shorter than the duration of the dozing state from the time when the dozing time measuring device starts to detect the dozing state until the second warning output device starts to warn the driver by outputting a dozing warning.

8. A warning method comprising:
detecting an inattentive state of a driver;
detecting at least one of a dozing state of the driver and a state in which the eyes of the driver are closed;
measuring a duration of the inattentive state of the driver;
measuring at least one of a duration of the dozing state of the driver and a time during which the eyes of the driver are closed; and
issuing a warning to the driver,
wherein the period of time from the time that the inattentive state is detected until time that the warning is issued is shorter than the period of time from the time that at least one of the dozing state of the driver and the state in which the eyes of the driver are closed is detected until the time that the warning is issued, and
wherein the on-board warning device is configured such that the duration of the inattentive state from the time when the inattentive time measuring device starts to detect the inattentive state until the first warning output device starts to warn the driver by outputting an inattentive warning is shorter than the duration of the dozing state from the time when the dozing time measuring device starts to detect the dozing state until the second warning output device starts to warn the driver by outputting a dozing warning.

9. The on-board warning apparatus according to claim 2, wherein the dozing time measuring device measures a duration of a state in which the eyes of the driver are closed as the dozing time.

10. The on-board warning apparatus according to claim 2, wherein the inattentive time measuring device measures a duration of a state in which the driver is not facing forward as the inattentive time.

11. The on-board warning apparatus according to claim 3, wherein the inattentive time measuring device measures a duration of a state in which the driver is not facing forward as the inattentive time.

12. The on-board warning apparatus according to claim 4, wherein the inattentive time measuring device measures a duration of a state in which the driver is not facing forward as the inattentive time.

13. The on-board warning apparatus according to claim 5, wherein the inattentive time measuring device measures a duration of a state in which the driver is not facing forward as the inattentive time.

14. The on-board warning apparatus according to claim 2, wherein a change curve of the predetermined threshold value for the inattentive time is convex and a change curve of the predetermined threshold value for the dozing time is concave, and wherein the change curve of the predetermined threshold value for the inattentive time and the change curve of the predetermined threshold value for the dozing time represent changes in the value of the predetermined threshold values for the inattentive time and the value of the predetermined threshold values for the dozing time, respectively, plotted over time.

15. The on-board warning apparatus according to claim 5, wherein a change curve of the predetermined threshold value for the inattentive time is convex and a change curve of the predetermined threshold value for the dozing time is concave, and wherein the change curve of the predetermined threshold value for the inattentive time and the change curve of the predetermined threshold value for the dozing time represent changes in the value of the predetermined threshold values for the inattentive time and the value of the predetermined threshold values for the dozing time, respectively, plotted over time.

* * * * *